United States Patent
Gochanour

(10) Patent No.: US 6,604,660 B2
(45) Date of Patent: Aug. 12, 2003

(54) DISPENSER FOR FLEXIBLE HAND COVERINGS

(76) Inventor: G. Gary Gochanour, 3108 Baker Rd., Dexter, MI (US) 48130

(*) Notice: Subject to any disclaimer, the term of this patent is extended or adjusted under 35 U.S.C. 154(b) by 197 days.

(21) Appl. No.: 09/852,693

(22) Filed: May 10, 2001

(65) Prior Publication Data

US 2002/0166883 A1 Nov. 14, 2002

(51) Int. Cl.[7] .............................................. B25C 11/02
(52) U.S. Cl. .......................... 225/90; 156/510; 128/879
(58) Field of Search ............................... 225/20, 85, 51, 225/47, 54, 76; 83/614; 128/82; 156/212, 247, 475, 510, 529, 538, 543

(56) References Cited

U.S. PATENT DOCUMENTS

| | | | |
|---|---|---|---|
| 526,038 A | 9/1894 | Hoke | 225/89 |
| 767,233 A | 8/1904 | McCourt | |
| 1,332,194 A | 3/1920 | Areus | |
| 1,486,006 A | 12/1924 | Blom | |
| 1,731,340 A | 10/1929 | Lambert | 2/158 |
| 2,311,363 A | 2/1943 | Bevier | 164/84.5 |
| 2,576,404 A | 11/1951 | Krueger | 242/55.5 |
| 2,577,284 A | 12/1951 | Steinle | 2/169 |
| 2,617,198 A | 11/1952 | Sharpe | 225/14 |
| 2,751,592 A | 6/1956 | Longstreth et al. | 2/21 |
| 2,773,264 A | 6/1956 | Nover | 2/159 |
| 2,864,090 A | 12/1958 | Sutherland | 2/161.7 |
| 2,954,910 A | * 10/1960 | Moncrieff | 225/20 |
| 3,035,345 A | 5/1962 | Barnard | 225/14 |
| 3,229,875 A | 1/1966 | Stoller | 2/169 |
| 3,260,260 A | 7/1966 | Questel | 128/132 |
| 3,387,307 A | 6/1968 | Blatz | 2/167 |
| 3,645,835 A | 2/1972 | Hodgson | 161/146 |
| 3,989,175 A | * 11/1976 | Cherrin | 225/76 |
| 4,017,907 A | 4/1977 | Margolis | 2/158 |
| 4,034,853 A | 7/1977 | Smith | 2/169 |
| 4,347,931 A | 9/1982 | Ginger et al. | 206/438 |
| 4,364,501 A | 12/1982 | Curtiss, Jr. | 225/19 |
| 4,454,974 A | * 6/1984 | Cooke | 225/106 |
| 4,607,774 A | 8/1986 | Garr | 225/47 |
| 4,804,432 A | 2/1989 | Jurrius et al. | 156/380 |
| 4,832,650 A | 5/1989 | Tong | |

(List continued on next page.)

FOREIGN PATENT DOCUMENTS

| | | | |
|---|---|---|---|
| DE | 4135973 | 5/1993 | 2/16 |
| FR | 2542980 | 9/1984 | 2/158 |
| WO | WO89/00385 | 9/1989 | 2/16 |

*Primary Examiner*—Allan N. Shoap
*Assistant Examiner*—Ghassem Alie
(74) *Attorney, Agent, or Firm*—Gifford, Krass, Groh, Sprinkle, Anderson & Citkowski, PC

(57) ABSTRACT

A dispenser is configured to receive a roll of thin, flexible film, preferably with an adhesive on one surface thereof, for use as a temporary hand covering. The film is drawn from the roll through rotation over a backing member such that the adhesive surface faces outwardly, enabling a user to place the palm and fingers of a hand against the film and backing member prior to severing the film into a sheet now adhered to the hand. The backing member itself preferably forms part of a compressible body enabling a user to squeeze the body through the film for improved adherence of the sheet to the hand. Various alternatives are disclosed for severing the film into individual sheets. The sheet itself may include lines of perforations, spaced apart along the roll at a distance sufficient to cover a hand. Additionally, the dispenser may include an element which the film is drawn past to cut the film. Such an element my be in the form of a blade having a knife edge or serrations, and maybe heated. Depending upon the configuration, such an element may be between the backing member and the roll or on the other side of the backing member with respect to the roll. A mechanism for preventing the roll from rotating is coupled to the backing member. Preferably, the backing member is moveable away from the roll, enabling a user to move the hand bearing against the film and backing member away from the roll to assist in severing the sheet from the roll.

16 Claims, 6 Drawing Sheets

U.S. PATENT DOCUMENTS

| | | | |
|---|---|---|---|
| 4,844,293 A | 7/1989 | McLaughlin | 221/34 |
| 4,847,918 A | 7/1989 | Sturm | 2/161 |
| 4,884,300 A | 12/1989 | Vistins | 2/162 |
| 4,913,897 A | 4/1990 | Chvapil et al. | 424/99 |
| 4,916,757 A | 4/1990 | Berlin et al. | 2/159 |
| 4,928,322 A * | 5/1990 | Bradfield | 2/169 |
| 4,938,515 A | 7/1990 | Fazio | 2/21 |
| 4,942,992 A | 7/1990 | Fischer et al. | 224/240 |
| 4,951,858 A | 8/1990 | Krall | 225/77 |
| 4,993,589 A | 2/1991 | McLaughlin | 221/33 |
| 5,012,801 A | 5/1991 | Feret | 128/155 |
| 5,018,516 A | 5/1991 | Gilman | 128/155 |
| 5,020,160 A | 6/1991 | Cano | 2/159 |
| 5,024,217 A * | 6/1991 | Spencer | 602/52 |
| 5,025,503 A | 6/1991 | O'Brien | 2/169 |
| 5,084,927 A | 2/1992 | Parkevich | 5/484 |
| 5,096,089 A | 3/1992 | McLaughlin | 221/26 |
| 5,172,424 A | 12/1992 | Adkins | 2/21 |
| 5,180,605 A | 1/1993 | Milner | 427/2 |
| 5,181,276 A | 1/1993 | Kersten et al. | 2/161 R |
| 5,190,197 A | 3/1993 | Novak | 224/312 |
| 5,210,880 A | 5/1993 | Yale | 2/159 |
| 5,322,201 A | 6/1994 | Garr | 225/47 |
| 5,456,354 A | 10/1995 | Wood | 206/278 |
| 5,534,346 A | 7/1996 | Robinson | 428/343 |
| 5,552,201 A | 9/1996 | Burgess et al. | 428/43 |
| 5,566,390 A | 10/1996 | Clancy | 2/16 |
| 5,573,168 A | 11/1996 | Kannankeril et al. | 225/46 |
| 5,575,014 A | 11/1996 | Kane et al. | 2/16 |
| 5,636,406 A | 6/1997 | Strong | 15/227 |
| 5,651,487 A * | 7/1997 | Hansen | 225/106 |
| 5,691,069 A | 11/1997 | Lee | 428/500 |
| 5,774,889 A | 7/1998 | Gochanour | 2/16 |
| 5,799,331 A | 9/1998 | Stewart | 2/158 |
| 5,864,883 A * | 2/1999 | Reo | 2/158 |
| 5,878,909 A | 3/1999 | Rogow | 221/45 |
| 5,921,434 A * | 7/1999 | Hollander et al. | 221/34 |
| 5,966,741 A | 10/1999 | Klecina | 2/169 |
| 5,975,083 A * | 11/1999 | Henderson, Jr. | 128/878 |
| 6,021,919 A * | 2/2000 | Kelly | 221/25 |
| 6,021,920 A | 2/2000 | Aldape | 221/96 |
| 6,112,936 A | 9/2000 | Arizmendi | 221/45 |
| 6,497,340 B2 * | 12/2002 | Grinberg | 221/45 |

\* cited by examiner

DISPENSER FOR FLEXIBLE HAND COVERINGS

FIELD OF THE INVENTION

This invention is related to protective hand coverings and particularly to dispensers for a protective hand covering formed from a sheet of thin flexible film which is temporarily bonded to the user's hand during use.

BACKGROUND OF THE INVENTION

In many fields, such as the dental, medical, food service, laboratory, and precision manufacturing fields, reducing the potential for contamination is a primary concern. Because workers in these fields routinely manually handle contaminated or contaminatable materials, it is critical that some type of barrier be interposed between the hands of the workers and the contaminated or contaminatable materials. Typically, this barrier comprises a latex or plastic film glove or mitten. The user places their hand into the glove or mitten prior to handling the contaminated or contaminatable materials and this prevents contamination from being transferred to or from the substance or object being handled.

There are primarily three routes for the transfer of contaminates. The first route is the transfer of contaminates from the contaminated material to the user handling the contaminated material. In the dental, medical and other health care fields, the AIDS epidemic has heightened awareness of the possibility of patients infecting their health care workers with the HIV virus through exposure to body fluids. Even before AIDS was a concern, however, the presence of other highly contagious infectious agents, such as hepatitis, justifiably caused serious concerns among health care workers and resulted in procedures and precautions being implemented for reducing this possible route of contamination. For industrial and laboratory workers handling toxic or hazardous materials, particularly persistent toxins such as mercury, lead and pesticides, extreme precautions are taken to avoid any worker exposure to these materials.

A second route is the transfer of contaminates from the user to the contaminatable object or materials being handled. Some types of computer and electrical components, such as disk drive storage media and halogen light bulbs, can be ruined by being merely touched with an unprotected hand. Detectable amounts of oil, moisture, skin flakes, etc. will inevitably be transferred to any object which is handled with an unprotected hand. Laboratory samples and crime scene evidence are two other types of materials that can easily be contaminated if proper protective hand coverings are not worn.

A third route for contamination is the transfer of contaminates from an earlier object handled by a worker to a later object handled by that worker or a co-worker. This third route is often the most difficult to control because the contamination may be indirect (i.e. it may not be directly from the earlier object to the worker to the later object).

Health care workers typically remove their old gloves and put on new gloves prior to examining or treating a new patient. What may be overlooked, however, is that when their gloves become contaminated during examination or treatment of a patient, any object touched by these gloves, such as a door handle, a pen, a drawer handle, or treatment equipment, may itself become contaminated. When handling particularly virulent infectious agents, an attempt may made to use cleaning or sterilizing agents, such as chemical solutions, to remove or neutralize contaminates which have been transferred to these areas. Remedial measures, such as applying cleaning or sterilizing agents, are typically less than completely effective in eliminating contamination. Similar issues arise when industrial or laboratory workers handle toxic, hazardous or contaminated materials. The preferred method for eliminating this route for contamination is to eliminate the contamination of these areas altogether.

A primary reason these areas become contaminated is the difficulty of removing and putting on typical hand coverings. Typical hand coverings require that the hand or a portion of the hand be place inside and positioned with respect to a closed section of the hand covering. It can take a greater part of a minute to remove a contaminated pair of conventional latex gloves, replace them with a new pair and properly position the new gloves over the user's hands. If after handling potentially contaminated materials, a health care worker must operate treatment equipment, the worker must first remove their current pair of gloves and then put on a new pair of gloves before handling the equipment. To avoid accidentally contaminating the patient with contaminates that may have been present on the machine, the worker must then remove this second pair of gloves and put on a third pair of gloves before again coming into contact with the patient.

In my U.S. Pat. No. 5,774,889, I describe a protective hand covering for adhering to a user's hand. In the preferred embodiment, a pressure-sensitive adhesive is applied to the back surface of a sheet of thin flexible film. The pressure-sensitive adhesive provides a sufficiently strong bond to prevent the hand covering from being inadvertently dislodged, but a sufficiently weak bond to allow the hand covering to be removed without injuring the user. The film is sufficiently impervious to contaminates to prevent the transfer of contaminates from the substance or object being handled to the user, and vice versa.

As disclosed in the '889 patent, the entire contents of which are incorporated herein by reference, several methods for packaging and dispensing protective hand coverings are feasible. For example, a stack of protective hand coverings may be packaged in a tablet or fan-fold format. The hand coverings could also be dispensed from a continuous roll mounted in a holder. The importance of the dispenser is that by substantially decreasing the time it takes to remove and put on hand coverings, the time required to perform certain types of procedures can be dramatically reduced. Increasing the ease of putting on (and removing) hand coverings will also encourage workers to put on new hand coverings more frequently, which will in turn reduce the likelihood of indirect contamination.

SUMMARY OF THE INVENTION

This invention is directed to a dispenser for receiving a roll of thin, flexible film for use as a temporary hand covering. Preferably such a film includes an adhesive on one surface thereof. The preferred dispenser includes a backing member over which film may be drawn from the roll through rotation such that the adhesive surface faces outwardly, enabling a user to place the palm and fingers of a hand against the film and backing member prior to severing the film into a sheet now adhered to the hand. The backing member itself preferably forms part of a compressible body enabling a user to squeeze the body through the film for improved adherence of the sheet to the hand.

Various mechanisms may be used alone or in combination to sever the film into an individual sheet. The sheet itself may include lines of perforations, spaced apart along the roll at a distance sufficient to cover a hand. Additionally, the dispenser may include an element which the film is drawn past to cut the film. Such an element my be in the form of a blade having a knife edge or serrations, and maybe heated. Depending upon the configuration, such an element may be between the backing member and the roll or on the other side of the backing member with respect to the roll.

The dispenser may further include a mechanism for preventing the roll from rotating while the film is severed into a sheet. Such a mechanism may also be coupled to the backing member. In the preferred embodiment, the backing member is moveable away from the roll, enabling a user to move the hand bearing against the film and backing member away from the roll to assist in severing the sheet from the roll.

DETAILED DESCRIPTION OF THE INVENTION

As discussed above, this invention relates to apparatus for dispensing flexible hand coverings, particularly of the type described in U.S. Pat. No. 5,774,889. Although the preferred embodiment is ideally suited to the dispensing of thin, flexible hand coverings which are perforated and have at least tacky or adhesive surface, it will be apparent to those of skill in the art that both perforated and non-perforated sheets, and sheets having no adhesive, or an adhesive on both sides, may be accommodated by the invention, particularly through the alternative embodiments described herein.

Figure 1:
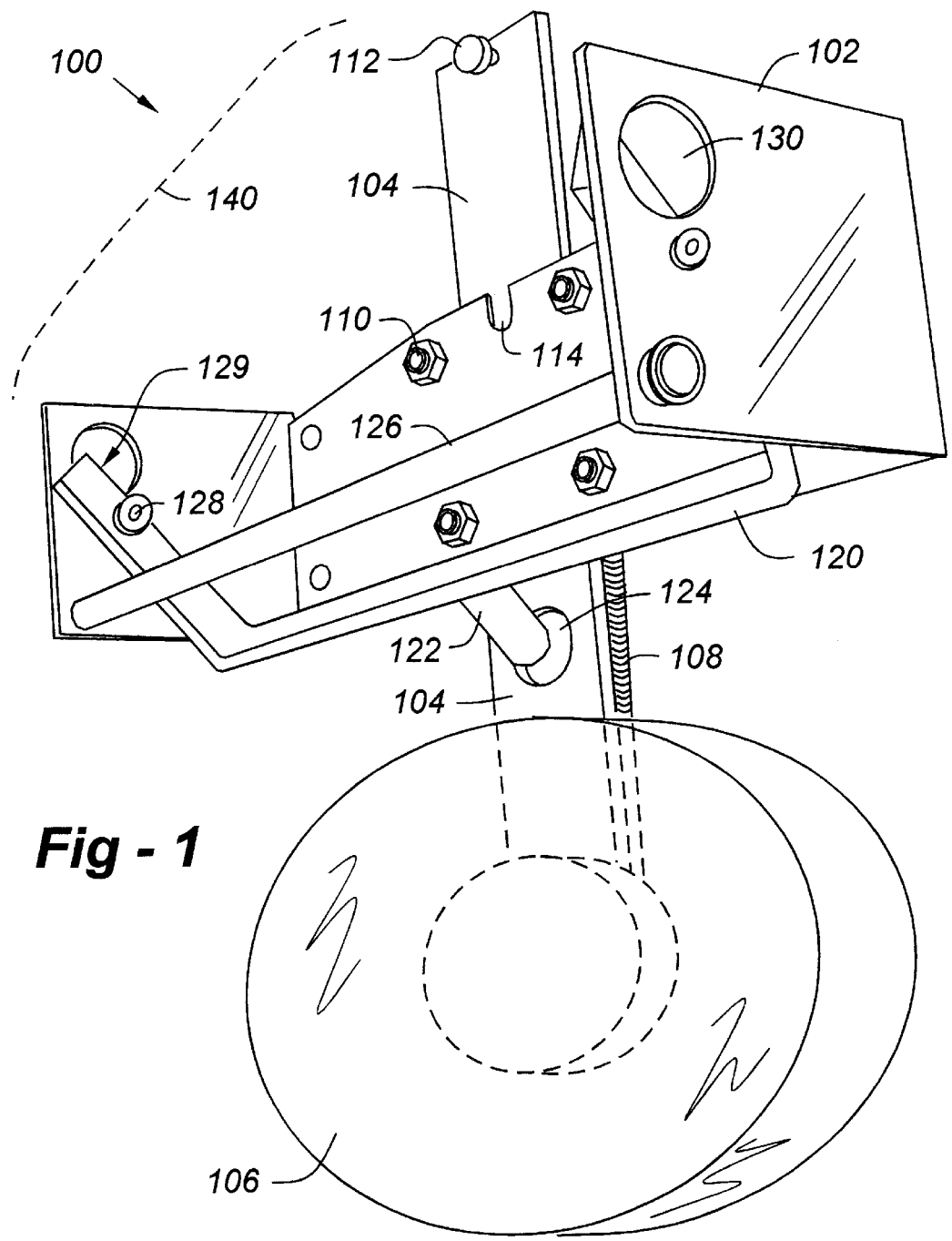
FIG. 1 is a perspective view of a preferred embodiment of the invention.

A preferred embodiment is depicted generally at 100 in FIG. 1. The unit includes a bracket 102 having bent sides with holes 130 to receive a roll of hand covering, as depicted in subsequent drawings. A vertical member 104 is journaled onto, and preferably behind, the rear portion of bracket 102. Using rollers visible in FIG. 2 secured by fasteners 110.

A tab of compressible material is mounted onto the vertical member 104, preferably using some spacer to hold the pad 106 away from the surface of the member 104. For example, the lower portion of the member 104 may be angled, or blocks of wood or plastic may be utilized for such purpose. Note that the pad 106 is shown as an oval in FIG. 1, but as a square in subsequent figures. This was done to make the point that the pad 106 may be in any suitable shape, including dome-shaped, football-shaped, and so forth, with any suitable periphery. The pad itself may be composed of any suitable compressible material, including foams, gels, and the like, in the lower portion of the member 104, including the pad 106, may be contained in a removable protective bag or bladder (not shown) to keep the pad clean. Such a bag or bladder may be removable, replaceable and/or washable to further ensure cleanliness.

The vertical member 104 preferably further includes a stop 112 which is received by an indent 114 in the back side of the bracket 102, and an aperture 124 to receive a post 122, coupled to an angled stop bar 120. The stop bar 120 is hingedly mounted to the sides of the bracket 102 through fasteners 128, and the ends of the sop bar 120 include edges 129 that engage with and retain the roll, as described in further detail below.

Figure 2:
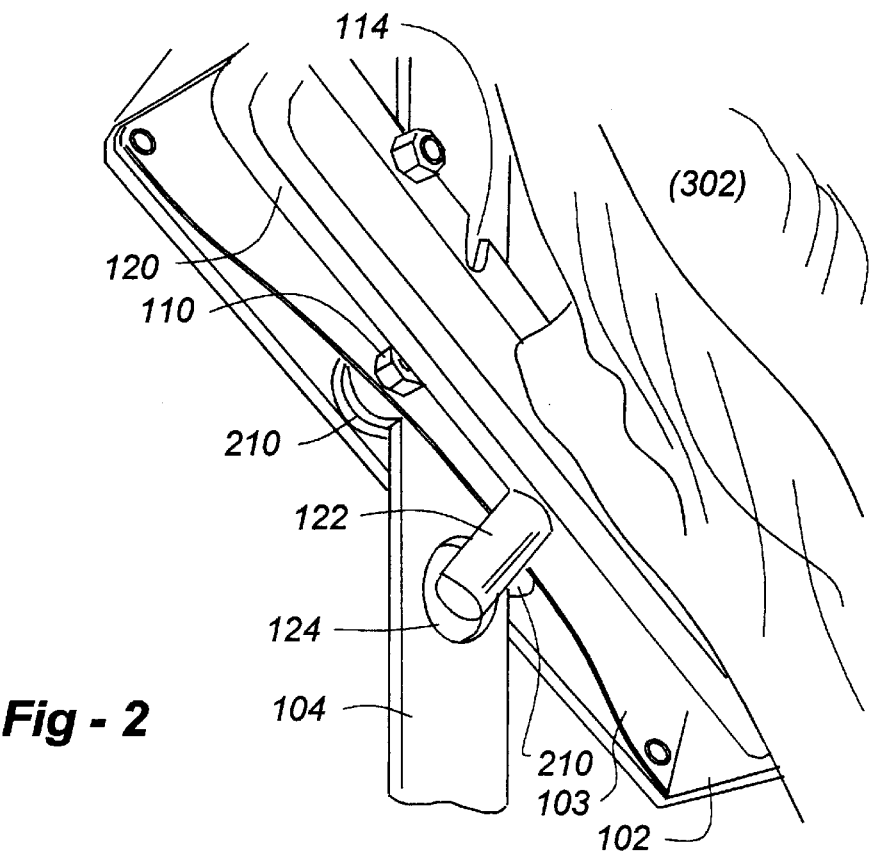
FIG. 2 is a perspective view of a portion of the preferred embodiment, taken from below to better illustrate a carriage mechanism.

FIG. 2 is a perspective view better illustrating the underside of the bracket 102, particularly where the vertical member 104 engages therewith. This view betters shows the way in which a curved piece of metal 103 is used to form a space to receive the vertical member 104, enabling rollers 210 held by fasteners 110 slidingly engage with the sides of the vertical member 104. Note that post 122 is able to protrude into aperture 124, such that stop bar 120 does not retain the roll of flexible material 302.

Figure 3:
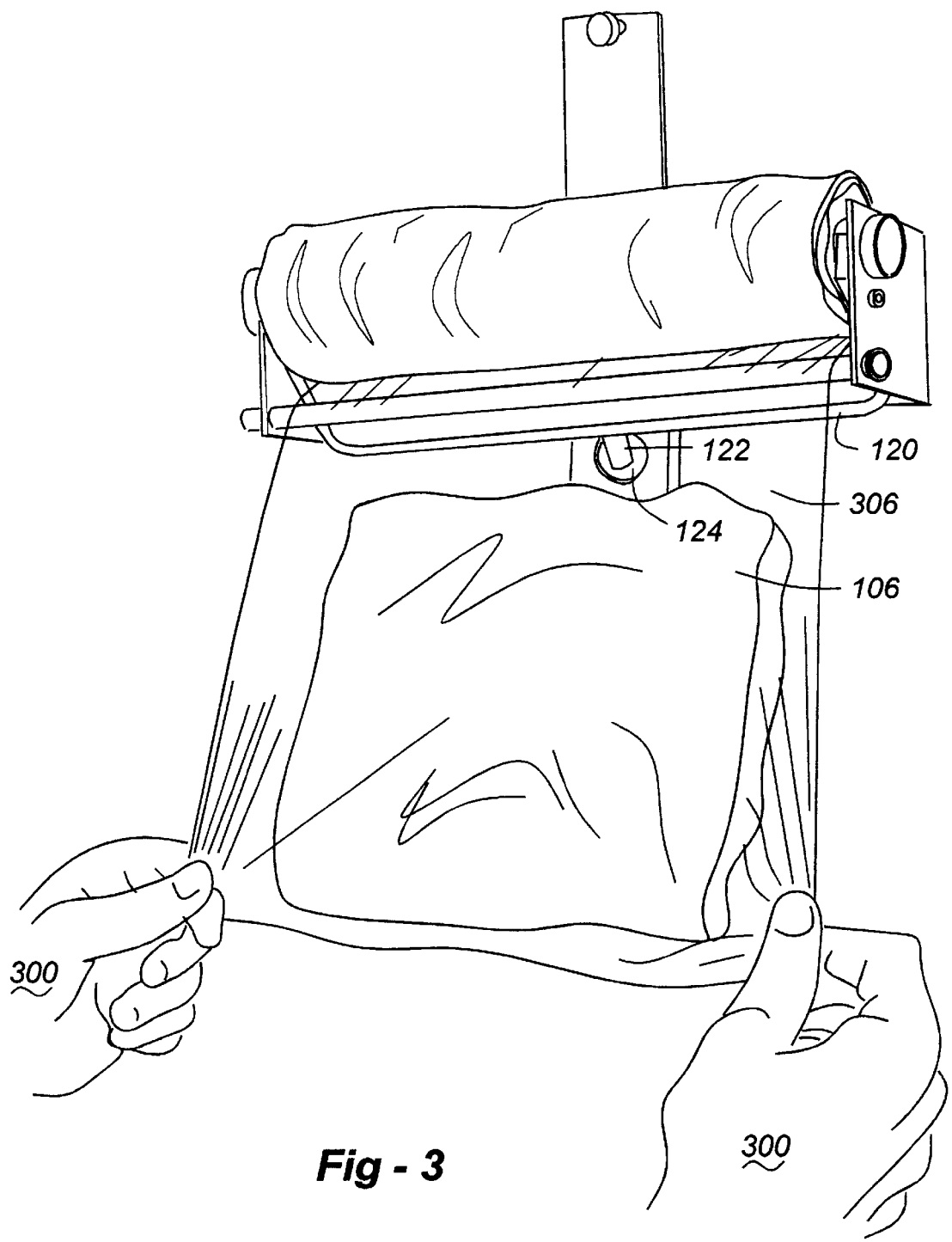
FIG. 3 is a drawing which illustrates an initial step associated with using a dispenser according to the invention.

FIG. 3 is the first drawing of a series used to show the way in which the apparatus is used. The person uses his or her hands 300 to pull a section 306 of the roll 302 down over the compressible pad 106. The roll 302 is placed in the dispenser such that it is drawn from below and behind over the element 126. When the vertical member 104 is in an upward position, with post 122 being received by aperture 124, allowing the roll 302 to freely move as the user draws the sheet 306 over the compressible pad 106.

Figure 4:
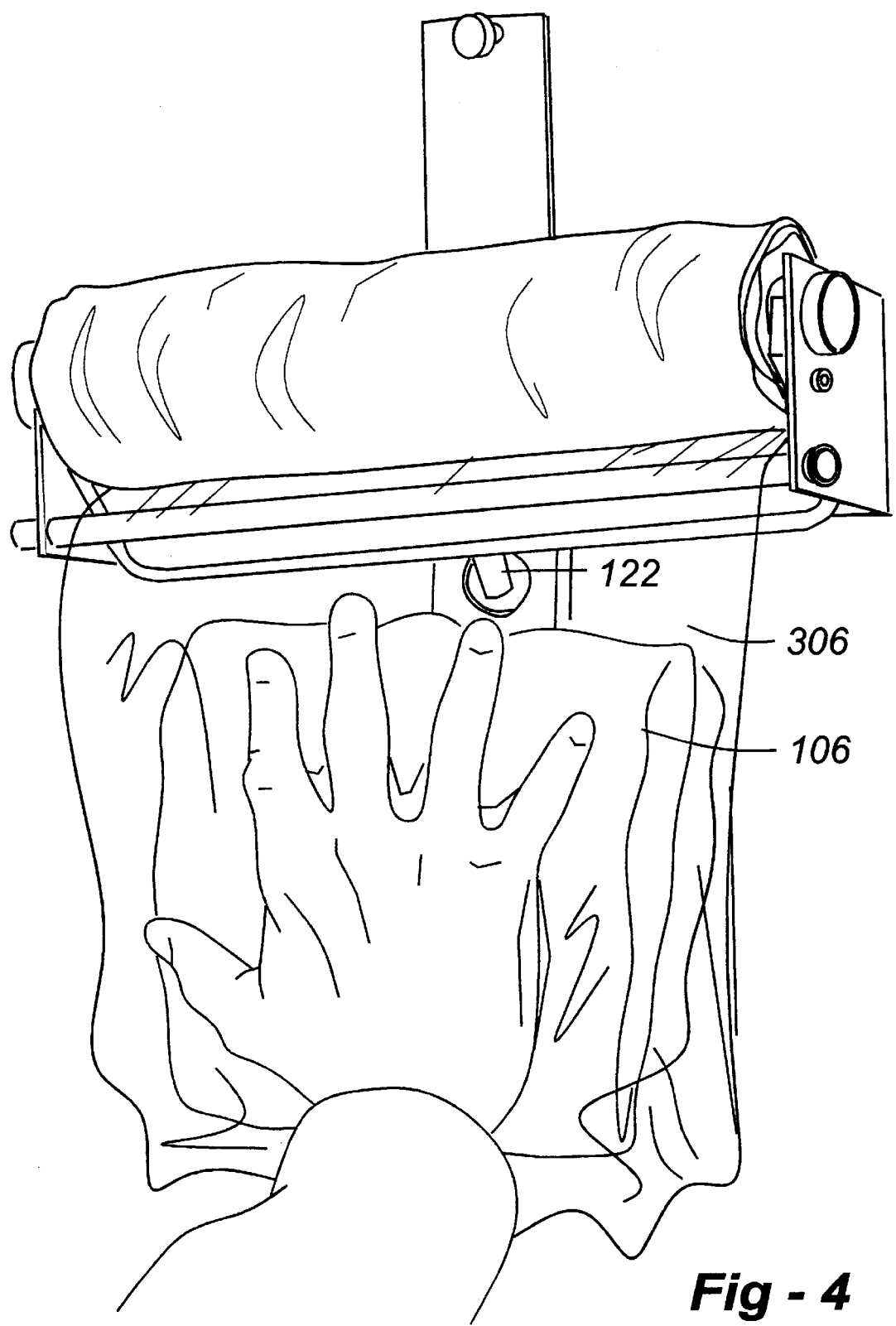
FIG. 4 is a drawing which illustrates an intermediate step associated with the use of the invention, wherein a user's hand is placed against the protective film drawn over a compressible backing.
Figure 5:
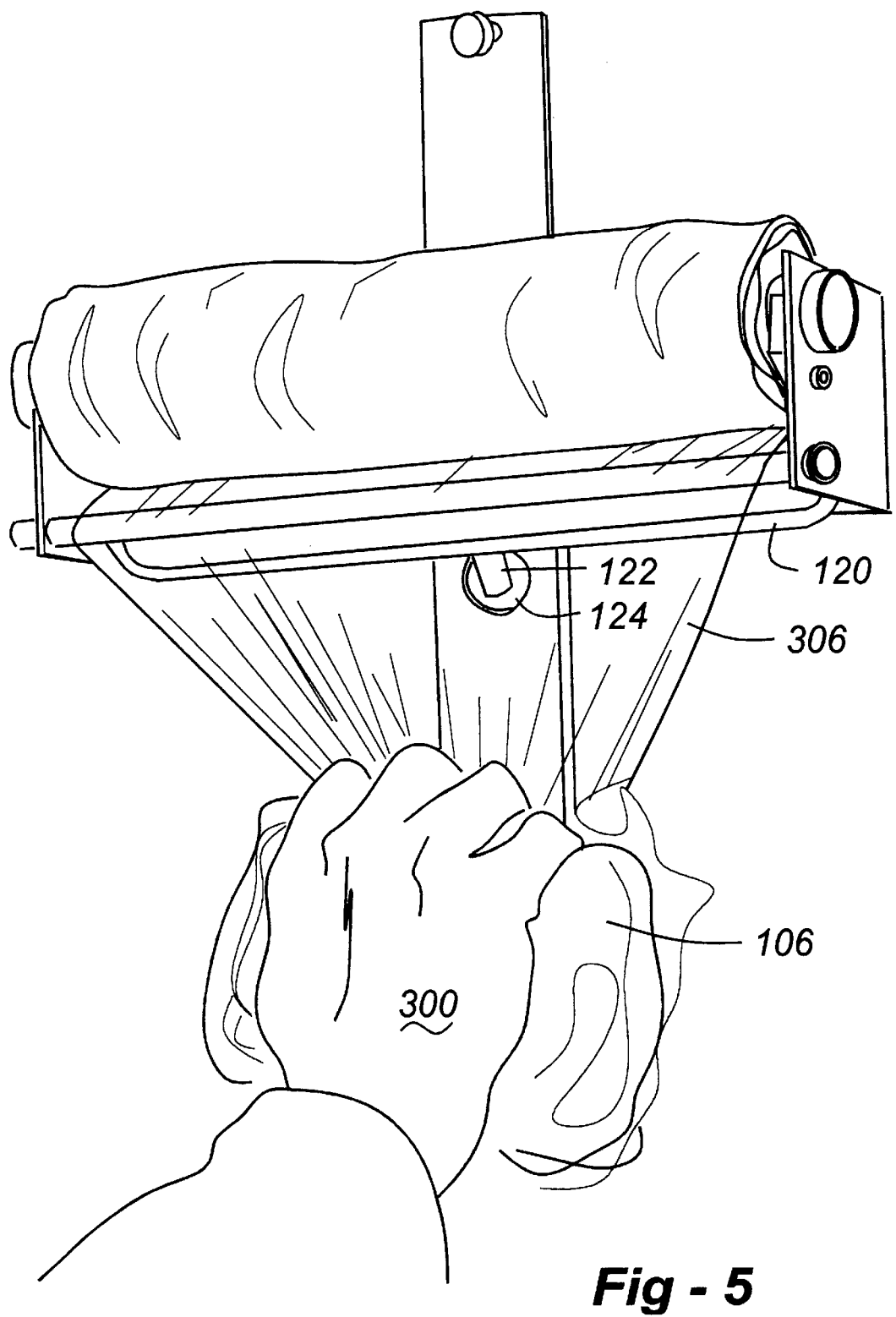
FIG. 5 shows how a user squeezes the compressible backing through the film prior to separating the film from the roll.

Having pulled the sheet 306 over the pad 106, the user 300 places his or her hand onto the drawn sheet, as shown in FIG. 4, then squeezes the pad 106 through the sheet, as shown in FIG. 5. Post 122 is still received by the aperture 124, enabling the roll to dispense the relatively minor additional amount of material, if necessary.

Figure 7:
FIG. 7 is a drawing which shows a hand covering properly applied to the hand of a user.
Figure 6:
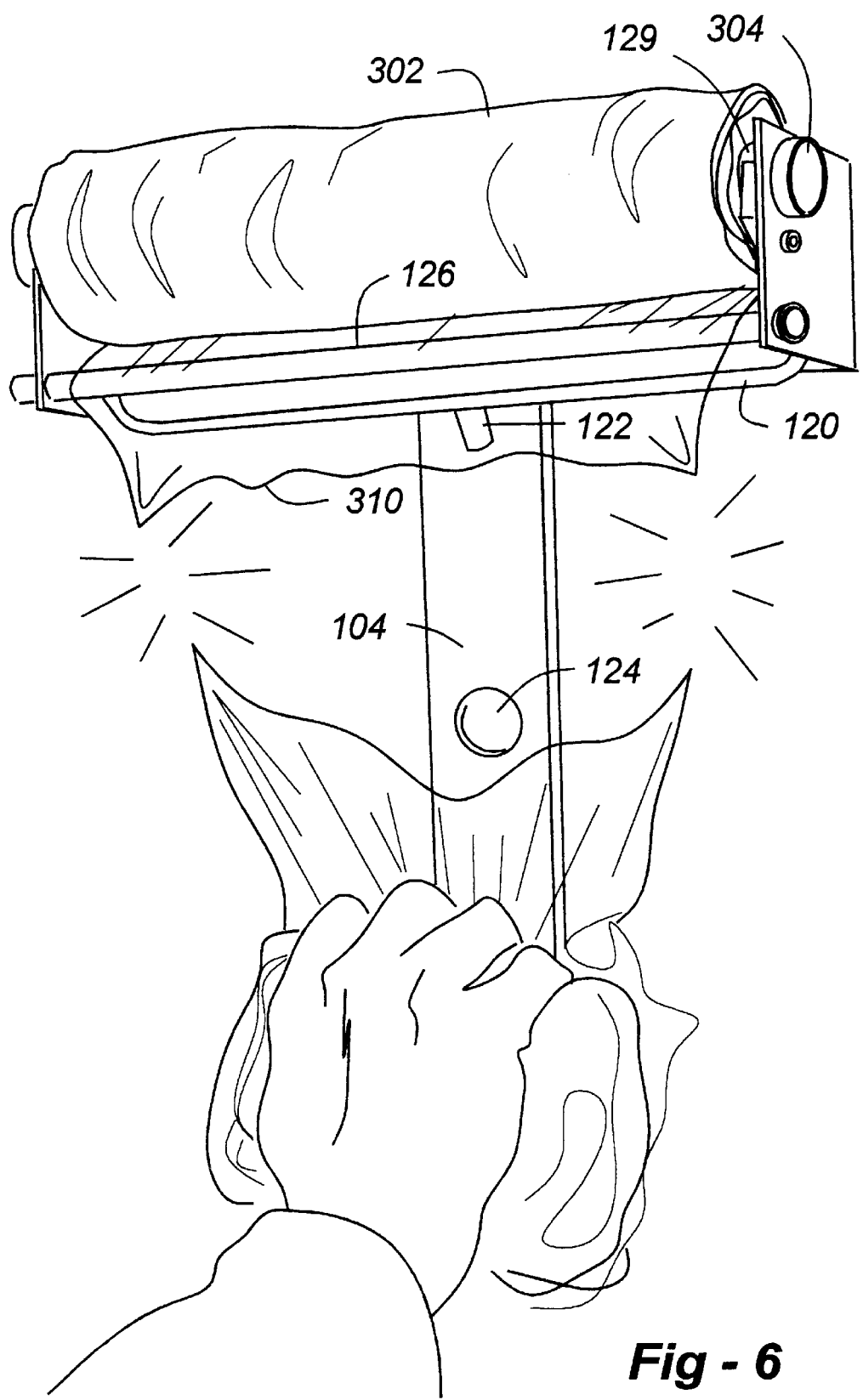
FIG. 6 is a drawing which shows how the user holds the compressible member and film downwardly to sever an individual hand covering from the roll.

While squeezing the pad 106 through the drawn sheet, the user then pulls the pad downwardly, as shown in FIG. 6. As the pad is rigidly coupled to the vertical member 104, this causes the post 122 to leave the aperture 124, and further causes the stop bar 120 to pivot such that the edges 129 now compress against the sides of the roll form 304, thereby preventing any further rotational movement of the roll 302. With the roll 302 locked in position, movement of the hand and vertical member 104 downwardly causes the sheet to shear at a perforation 310 which, though difficult to see in the figures, is present nevertheless. This leaves a small amount of material hanging over the element 126, that that when the vertical member 104 is automatically returned to its original position by virtue of return springs 108 shown in FIG. 1, the apparatus is ready to dispense the next sheet. As shown in FIG. 7, with the sheet now adhered to the palmar surface of the user's hand, due to the squeezing action of the compressible pad, the film nearly covers the hand and sides of the fingers when the hand is removed from the dispenser apparatus. By simply folding any loose salvage around the to back surface of the hand, a rapid, clean covering is expressly provided. Of course, either hand of a user may be covered, with the process just described being essentially the same for the other hand. Although the invention has been described with reference to a roll 302 of film having spaced-apart perforations, it will be appreciated that if element 126 were able to sever the sheet, perforations might not be necessary. For example, element 126 may be a sharp and/or serrated blade, or may be an instantly heated wire activated when the user squeezes the pad. In addition, although the flexible material preferably includes a tacky adhesive which faces outwardly from the pad 106 when properly positioned, static cling alone may be sufficient with certain materials to cover the hand, thereby obviating the need for an adhesive. Alternatively, if it is desired that some form of adhesive be placed on the outward surface of the covered hand, the same or different adhesives may be placed on both sides of the sheet, and the apparatus would work just as well, though the pad 106 may need to be covered with a non-stick surface such as Teflon or other material. Finally, though the dispenser and sheet are preferably vertically oriented, it will be appreciated that the apparatus may function in different orientations, including horizontally, or at different angles.

I claim:

1. A dispenser to receive a roll of thin, flexible film having an adhesive on one surface thereof for use as a temporary hand covering, the dispenser comprising:
    a backing member forming part of a compressible body over which film may be drawn from the roll through rotation such that the adhesive side of the film faces outwardly, enabling a user to place the palm and fingers of a hand against the film and backing member and squeeze the body through the film for improved adherence of the sheet to the hand; and
    means for severing the film into a sheet adhered to the hand.

2. The dispenser of claim 1, wherein the means for severing the film into a sheet includes a line of perforations in the film.

3. The dispenser of claim 1, wherein the means for severing the film includes an element which the film is drawn past to cut the film.

4. The dispenser of claim 3, wherein the element is a blade.

5. The dispenser of claim 3, wherein the element is serrated.

6. The dispenser of claim 1, further including a mechanism for preventing the roll from rotating while the film is severed into the sheet.

7. The dispenser of claim 6, wherein the mechanism for preventing the roll from rotating is coupled to the backing member.

8. The dispenser of claim 7, wherein the backing member is moveable away from the roll, enabling a user to move the hand bearing against the film and backing member away from the roll to assist in severing the sheet from the roll.

9. A hand covering system, comprising:
    a roll of thin, flexible film having an adhesive on one surface thereof; and
    a dispenser to receive the roll of film, the dispenser including:
        a backing member forming part of a compressible body over which film may be drawn from the roll through rotation with the adhesive side facing outwardly, thereby enabling a user to place the palm and fingers of a hand against the film and backing member and squeeze the body through the film for improved adherence of the sheet to the hand; and
        means for severing the film into a sheet adhered to the hand.

10. The system of claim 9, wherein the means for severing the film into a sheet includes a line of perforations in the film.

11. The system of claim 9, wherein the means for severing the film includes an element which the film is drawn past to cut the film.

12. The system of claim 11, wherein the element is a blade.

13. The system of claim 11, wherein the element is serrated.

14. The system of claim 9, further including a mechanism for preventing the roll from rotating while the film is severed into the sheet.

15. The system of claim 14, wherein the mechanism for preventing the roll from rotating is coupled to the backing member.

16. The system of claim 15, wherein the backing member is moveable away from the roll, enabling a user to move the hand bearing against the film and backing member away from the roll to assist in severing the sheet from the roll.

\* \* \* \* \*